United States Patent
Coates

(10) Patent No.: US 9,872,800 B2
(45) Date of Patent: Jan. 23, 2018

(54) DIAPER WITH POCKETED SLING AND STRETCHABLE COVER

(71) Applicant: Tailored Technologies, Inc., Winston-Salem, NC (US)

(72) Inventor: Fredrica V. Coates, Winston-Salem, NC (US)

(73) Assignee: Tailored Technologies, Inc., Winston-Salem, NC (US)

( * ) Notice: Subject to any disclaimer, the term of this patent is extended or adjusted under 35 U.S.C. 154(b) by 377 days.

(21) Appl. No.: 14/473,427

(22) Filed: Aug. 29, 2014

(65) Prior Publication Data

US 2015/0065979 A1 Mar. 5, 2015

Related U.S. Application Data

(60) Provisional application No. 61/871,514, filed on Aug. 29, 2013.

(51) Int. Cl.
| | | |
|---|---|---|
| A61F 13/15 | (2006.01) | |
| A61F 13/20 | (2006.01) | |
| A61F 13/505 | (2006.01) | |
| A61F 13/62 | (2006.01) | |
| A61F 13/49 | (2006.01) | |

(52) U.S. Cl.
CPC ...... *A61F 13/505* (2013.01); *A61F 13/15268* (2013.01); *A61F 13/49004* (2013.01); *A61F 13/622* (2013.01)

(58) Field of Classification Search
CPC .......................... A61F 13/49004; A61F 13/505
See application file for complete search history.

(56) References Cited

U.S. PATENT DOCUMENTS

| | | | | | |
|---|---|---|---|---|---|
| 2,292,030 | A | * | 8/1942 | Kraft | A41B 13/04 2/400 |
| 4,937,887 | A | * | 7/1990 | Schreiner | A44B 18/00 2/237 |
| 5,217,447 | A | * | 6/1993 | Gagnon | A61F 13/505 2/400 |
| 5,360,422 | A | * | 11/1994 | Brownlee | A61F 13/49004 604/385.14 |
| 5,930,875 | A | * | 8/1999 | Schreiner | A44B 18/00 24/442 |
| 2001/0034510 | A1 | * | 10/2001 | Shinkai | A61F 13/15211 604/385.01 |
| 2008/0215027 | A1 | * | 9/2008 | Labit | A61F 13/49004 604/378 |
| 2009/0299313 | A1 | * | 12/2009 | Knightingale | A61F 13/15268 604/367 |
| 2010/0036353 | A1 | * | 2/2010 | Payne | A61F 13/505 604/385.08 |
| 2010/0318057 | A1 | * | 12/2010 | Yakem | A61F 13/505 604/396 |

(Continued)

*Primary Examiner* — Michele M Kidwell
(74) *Attorney, Agent, or Firm* — Shumaker, Loop & Kendrick, LLP

(57) ABSTRACT

A diaper assembly including a diaper including hook fasteners positioned beneath and concealed by covers constructed from resiliently stretchable material, and a pocketed sling configured to removably attach to the diaper, the pocketed sling including loop fasteners arranged to removably attach to the hook fasteners concealed beneath the covers, thereby concealing attachment points between the diaper and the pocketed sling.

11 Claims, 4 Drawing Sheets

(56) References Cited

U.S. PATENT DOCUMENTS

2011/0301561 A1* 12/2011 Tournier .............. A61F 13/505
  604/377
2012/0116339 A1* 5/2012 Labit ................ A61F 13/49004
  604/372

* cited by examiner

DIAPER WITH POCKETED SLING AND STRETCHABLE COVER

CROSS-REFERENCE TO RELATED APPLICATION

This application claims priority from U.S. Patent Application No. 61/871,514 filed on Aug. 29, 2013, the entirety of which is incorporated herein by reference.

TECHNICAL FIELD AND BACKGROUND OF THE INVENTION

The present invention relates generally to the field of reusable diapers, and more particularly, to a diaper including a removable pocketed sling, removable absorbent pad and stretchable covers for concealing hook and loop fasteners used to attach the pocketed sling to the diaper, among other features.

Diapers are a well-known type of underwear that allows the wearer to defecate or urinate in a discreet manner, and are primarily worn by children who are not yet potty trained, adults that suffer from incontinence, the elderly, and those with physical or mental disabilities. When diapers become soiled they require changing, which is typically done by a parent or caregiver. Disposable diapers are typically made from synthetic materials and absorbent chemicals, while reusable diapers are typically made from cloth.

With regard to reusable diapers, to which the present invention is directed, conventional designs are inadequate for containing waste, do not stay in place, and require a change of the entire diaper regardless of the degree of soiling. These disadvantages result in wasted time and effort required to change the entire diaper, as well as unnecessary laundering and premature wear of unsoiled portions of the diaper. Therefore, what is a needed is a diaper provided in separable components that overcomes the disadvantages of conventional designs.

BRIEF SUMMARY OF THE INVENTION

In one embodiment, the present invention provides a diaper having hook fasteners concealed beneath covers constructed from resiliently stretchable material, and a pocketed sling having complementary loop fasteners configured to engage the fasteners beneath the covers to removably attach to the pocketed sling to the diaper. The pocketed sling may include at one end (i.e. the back) left and right laterally extending tabs carrying the loop fasteners, and at the other end (i.e., the front) one single elongate loop strip of loop fasteners. In an alternative embodiment, the diaper may be fitted with the loop fasteners and the pocketed sling may be fitted with the hook fasteners. In a specific embodiment, the hook fasteners of the diaper are located on the underside of the stretchable covers at the back of the diaper, and beneath the single stretchable cover at the front of the diaper.

In certain aspects, the diaper further includes a removable absorbent pad retained within the pocketed sling. Alternatively, the pocketed sling may include an absorbent pad integrally formed within the pocketed sling.

In certain aspects, the diaper includes at least one cover positioned on opposite sides of a same end portion of the diaper.

In certain aspects, the diaper includes two end portions in which at least one cover is positioned on opposite sides of each diaper end portion.

In certain aspects, the cover is constructed from resiliently stretchable material that includes a woven material, non-woven material, knitted material, or any combination thereof.

In certain aspects, the woven, non-woven, or knitted material includes nylon, rayon, cotton, polyester, a polyurethane-polyurea copolymer, or any combination thereof.

In certain aspects, the pocketed sling includes a first pocket formed on a front end of the pocketed sling and a second pocket formed on the rear end of the pocketed sling in which at least one of the pockets includes the left and right laterally extending tabs carrying loop fasteners thereon arranged to removably attach to the hook fasteners of the diaper beneath the covers.

In certain aspects, the pocketed sling includes a pocket formed on a front end of the pocketed sling and the rear end of the pocketed sling and each pocket includes the left and right laterally extending tabs carrying loop fasteners thereon arranged to removably attach to the hook fasteners of the diaper beneath the covers.

In certain aspects, the pocketed sling includes a cuff extending around the periphery of the sling, a main sling layer, and a pocket formed between the cuff and main sling layer.

In certain aspects, the pocketed sling includes a cuff extending around the periphery of the sling, a main sling layer, and two pockets formed between the cuff and main sling layer.

In certain aspects, the removable absorbent pad is positioned on the main sling layer, and each pocket is configured to receive and retain an end portion of the absorbent pad.

Also disclosed is a diaper including an outer diaper having hook fasteners concealed beneath covers constructed from resiliently stretchable material a pocketed sling configured to removably attach to the outer diaper, the pocketed sling including left and right laterally extending tabs carrying loop fasteners thereon arranged to removably attach to the hook fasteners of the outer diaper beneath the covers and a removable absorbent pad retained within the pocketed sling.

In certain aspects, the outer diaper includes at least one cover positioned on opposite sides of a same end portion of the outer diaper.

In certain aspects, the outer diaper includes two end portions in which at least one cover is positioned on opposite sides of each outer shell end portion.

In certain aspects, the cover includes a woven material, non-woven material, knitted material, or any combination thereof.

In certain aspects, the woven, non-woven, or knitted material includes nylon, rayon, cotton, polyester, a polyurethane-polyurea copolymer, or any combination thereof.

In certain aspects, the pocketed sling includes a first pocket formed on a front end of the pocketed sling and a second pocket formed on the rear end of the pocketed sling in which at least one of the pockets includes the left and right laterally extending tabs carrying loop fasteners thereon arranged to removably attach to the hook fasteners of the outer diaper beneath the covers.

In certain aspects, the pocketed sling includes a pocket formed on a front end of the pocketed sling and the rear end of the pocketed sling and each pocket includes the left and right laterally extending tabs carrying loop fasteners thereon arranged to removably attach to the hook fasteners of the outer diaper beneath the covers.

In certain aspects, the pocketed sling includes a cuff extending around the periphery of the sling, a main sling layer, and two pockets formed between the cuff and main sling layer, wherein the pockets are positioned at opposite ends of the sling.

In certain aspects, the removable absorbent pad is positioned on the main sling layer, and each pocket is configured to receive and retain an end portion of the absorbent pad.

In certain aspects, the outer diaper includes an elastic waistband and elastic leg cuffs positioned around the periphery of the outer diaper.

Embodiments of the invention can include one or more or any combination of the above features and configurations.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

BRIEF DESCRIPTION OF THE DRAWINGS

Features, aspects and advantages of the present invention are understood when the following detailed description of the invention is read with reference to the accompanying drawings, in which.

DETAILED DESCRIPTION OF THE INVENTION

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention. Like reference numbers refer to like elements throughout the various drawings.

Figure 1:
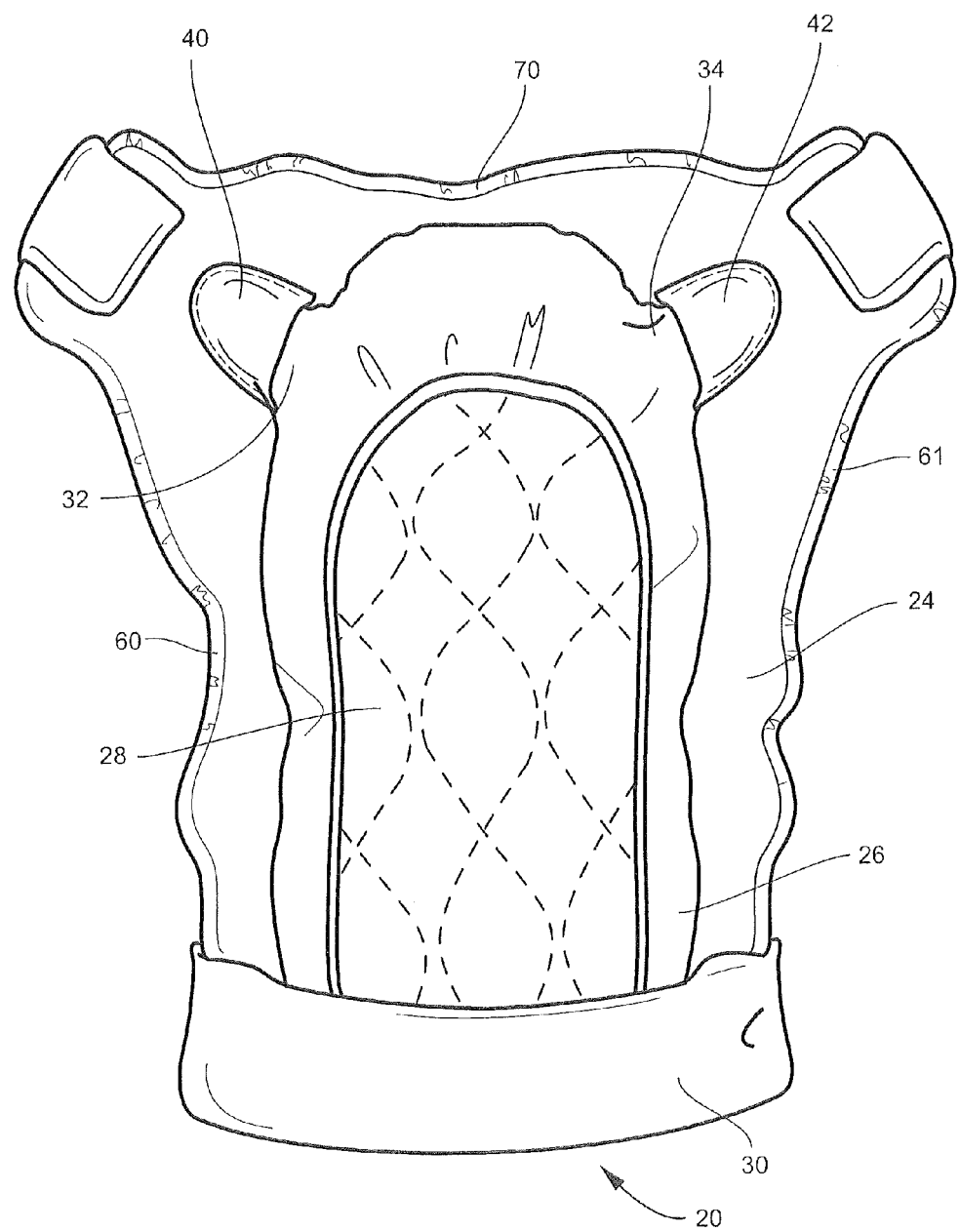
FIG. 1 illustrates a diaper and removably attachable pocketed sling according to preferred embodiments of the invention, wherein the attachment points of the two are concealed beneath covers for comfort.
Figure 2:
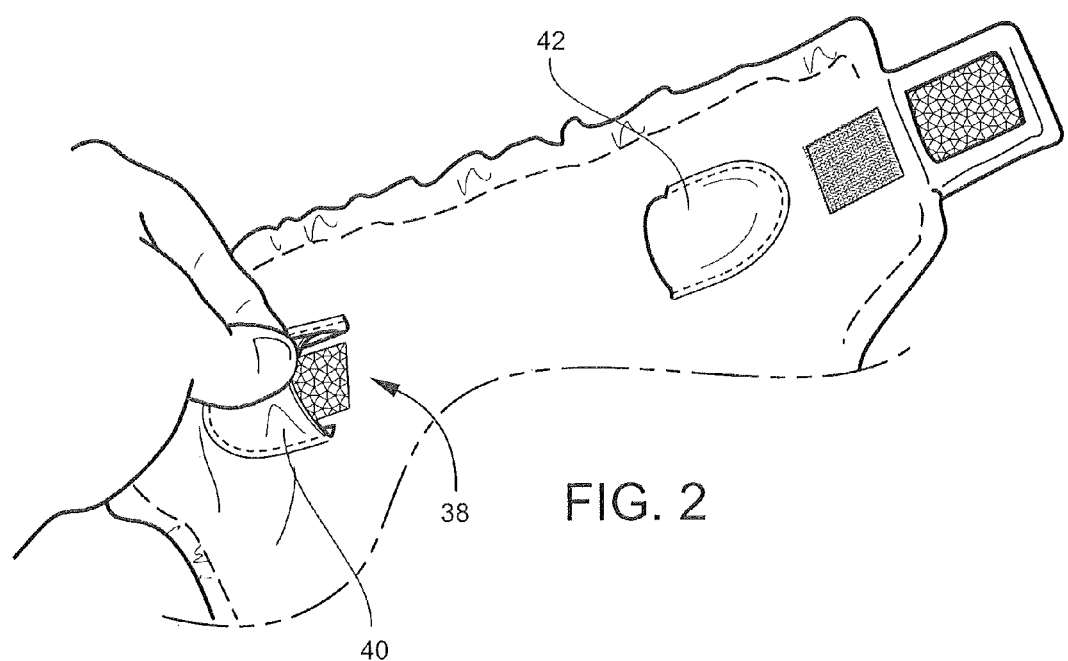
FIG. 2 is a detailed view of the diaper illustrating a stretch cover for concealing the hook and loop fasteners for attaching one tab of the pocketed sling to the diaper.
Figure 3:
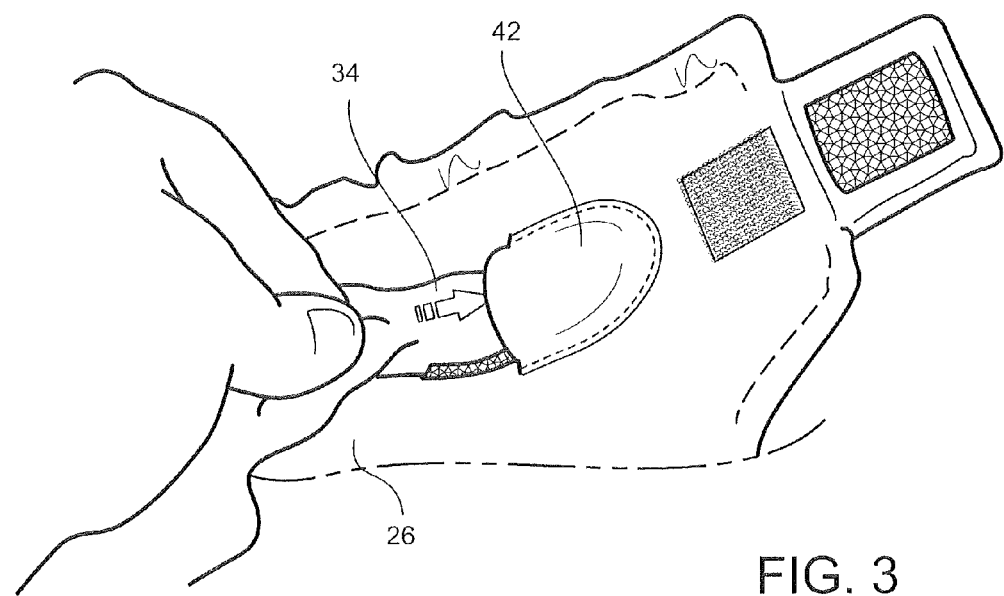
FIG. 3 is a detailed view of a portion of the infant diaper of FIG. 1 showing the stretch cover concealing the underlying hook and loop fastener attachment point.
Figure 4:
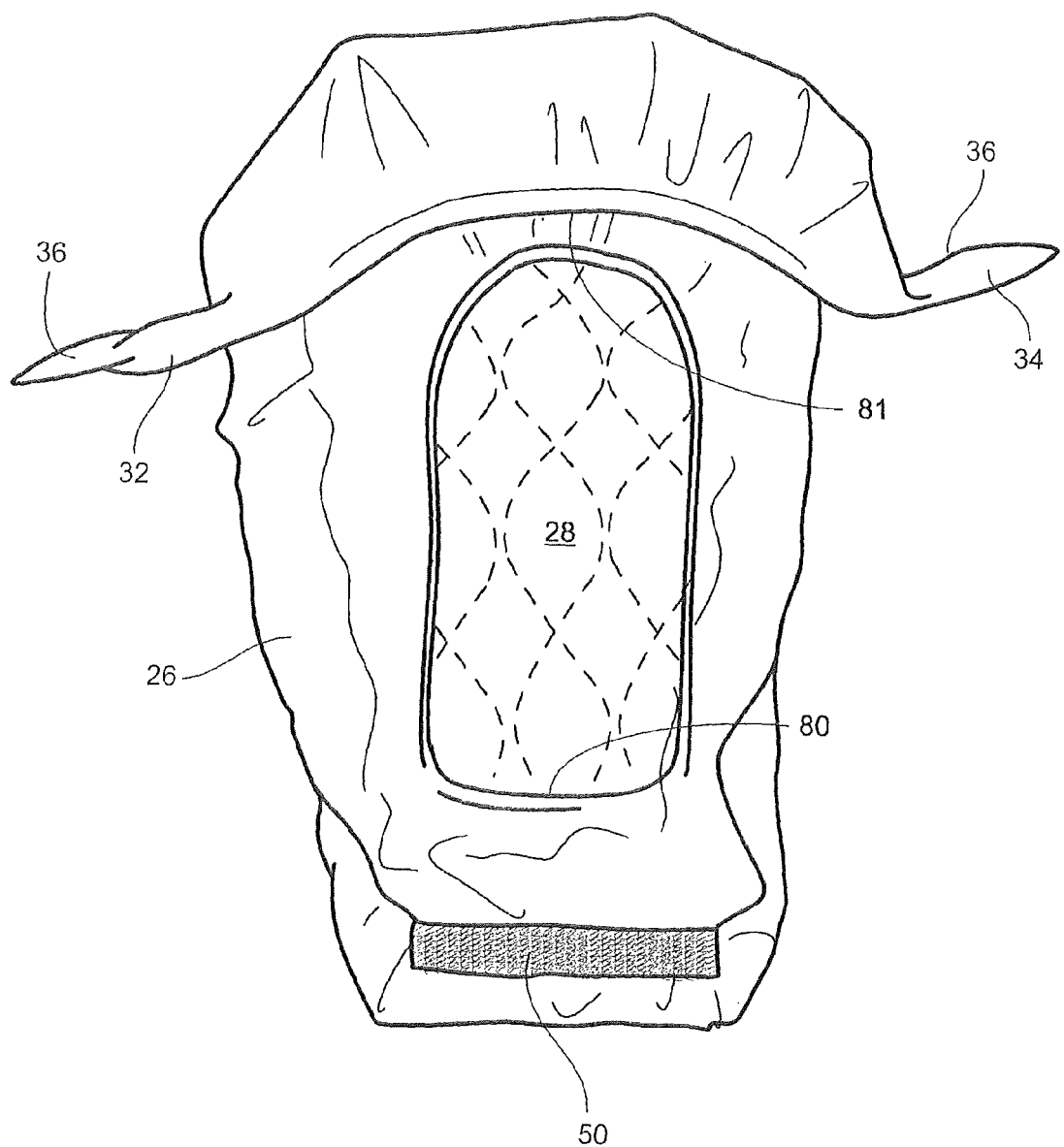
FIG. 4 is an isolated view of the removable pocketed sling showing the tabs for attaching the pocketed sling to the diaper.
Figure 5:
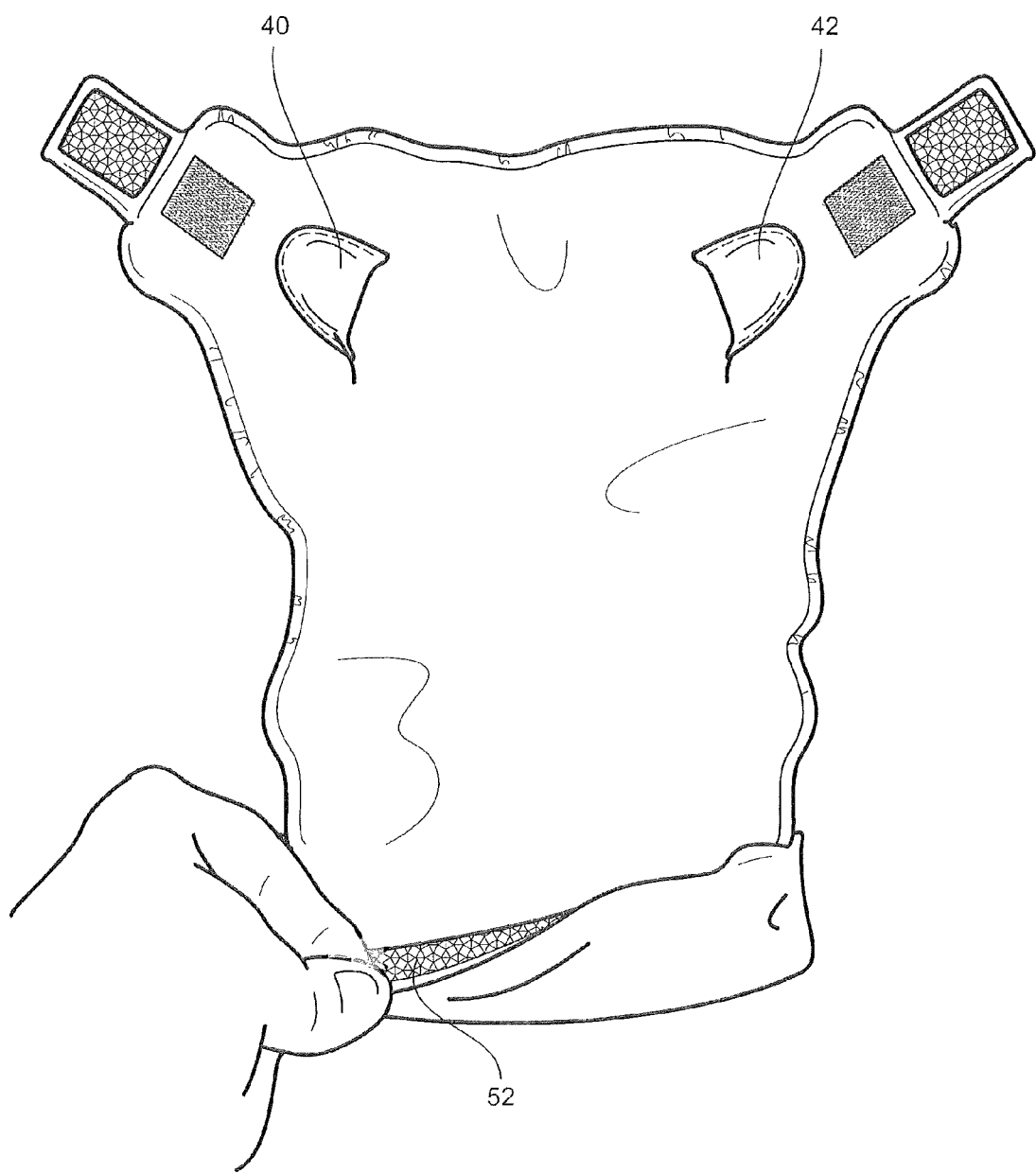
FIG. 5 is an isolated view of the diaper detailing a hook or loop fastener positioned on and spanning substantially the width of the front end of the diaper.

Referring to FIG. 1, an embodiment of an infant diaper having a removable pocketed sling is shown generally at reference numeral 20. The diaper 20 generally includes an outer diaper 24, and an inner pocketed sling 26 configured to be positioned between the outer diaper 24 and the infant. The pocketed sling 28 is configured to hold a removable absorbent pad 28.

The diaper 24 may be a multi-layered, cloth garment shaped to conform with and substantially cover the pelvic and posterior regions of the wearer. The diaper 24 has an hourglass shape and is fitted with elastic at the legs 60, 61 to closely conform to the wearer as a tertiary line of protection to contain feces and urine. The diaper 24 includes complementary hook and loop fasteners for securing the front and back flaps together around the wearer as known in a conventional diaper. The diaper 24 may further include an elastic waistband 70 to comfortably conform to the wearer's waist. As shown in FIG. 1, the front of the diaper 20 is shown at the bottom of the figure and the back (i.e., rear-end) of the diaper is shown at the top of the figure.

The pocketed sling 26 is removably attached to the diaper 24 using hook and loop fasteners, which may include, but are not limited to, VELCRO®. Specifically, the pocketed sling 26 is removably attached at its front and back to the diaper 24, while the mid-span portion of the pocketed sling remains detached from the diaper. The pocketed sling 26 is attached at its front to the outer diaper 24 by way of an elongate strip of hook or loop fasteners 50 located along the bottom of the pocketed sling and arranged to engage with a complementary hook or loop fastener 52 located concealed beneath an elongate cover 30 or "cuff" located at the front of the diaper 24. In certain aspects, the elongate strip of hook or loop fasteners 50 substantially spans the entire width of a portion of the pocketed sling to ensure proper and secure attachment of the pocketed sling to the diaper, and in certain aspects, the complementary hook or loop fasteners 52 located under the cover 30 or "cuff" located at the front of the outer diaper 24 substantially spans the entire width of the front end of the outer diaper 24.

When attaching the pocketed sling 26 to the diaper 24, the cover 30 is lifted or pulled aside to access the concealed hook or loop strip 52, and when the pocketed sling 26 is attached, the cover 30 conceals the fastener connection 50, 52 to provide comfort to the wearer. The cover 30 further conceals the hook or loop fasteners 52 during laundering to prevent the outer diaper from snagging on other articles.

Referring to FIGS. 1-4, the "back" of the pocketed sling 26 is also removably attached to the diaper 24 by way of hook and loop fasteners, however, the attachment is by way of left and right laterally-extending tabs 32, 34. The left and right tabs 32, 34 include hook or loop fasteners 36 attached to the bottom thereof that engage with complementary left and right hook or loop fasteners 38 at the back of the diaper 24. The left and right hook or loop fasteners 38 are located under left and right stretchable covers 40, 42 constructed from resiliently stretchable material.

In certain aspects, the stretchable covers cover may be a woven material, non-woven material, knitted material, or any combination thereof. Suitable examples of the resiliently stretchable material include, but are not limited to, lycra, spandex, polyester nylon, rayon, cotton or any combination thereof. In certain aspects, this stretchable material may include two-way stretch fabrics. The resiliently stretchable material may be able to stretch an additional 5 to 50%, 10 to 50%, 20 to 50%, 40 to 50%, 10 to 40%, 15 to 35% of the material's original dimensions while maintaining memory to return to its original shape/dimensions. The stretch covers 40, 42 conceal the hook and loop connections 36, 38 when made to provide comfort to the wearer, as well as conceal the hook connectors during laundering for the same reasons as discussed above with regard to the front cover 30.

In use, the stretchable covers 40, 42 are lifted "open" or pulled aside to expose the underlying hook fasteners 38. In an alternative embodiment, the hook fasteners 38 are located on the underside of the stretchable covers 40, 42 themselves. The left and right tabs 32, 34 are then pulled apart to engage the loop fasteners 36 with their respective hook fasteners 38. Once attached, the stretch covers 40, 42 are released, and the resiliency and memory of the stretch cover material returns the stretch covers to their original, substantially flat, wrinkle-free shape. The dimensional area, position, and shape of the stretch covers 38, 40 may vary based on the dimensions of the diaper components and location of the hook fasteners 38. By pulling the tabs 32, 34 apart in opposing directions and securing the tabs to their respective spaced apart hook counterparts, the pocketed sling 26 is held "open" and prevented from bunching, thus remaining better positioned to contain fecal matter, among other advantages.

In certain aspects, the diaper 24 may include a set of stretchable covers positioned on each of the front and back ends. These sets may include, for example, a cover positioned on opposite sides of each respective end (i.e., front end and back end) of the diaper such that the outer diaper includes four stretchable covers positioned on the diaper. As discussed above, each of these covers preferably conceal hook or loop fasteners. In this aspect, the pocketed sling may include a set of left and right laterally-extending tabs positioned on opposite ends of the pocketed sling. Each of these tabs preferably include hook or loop fasteners such that the each respective tab is configured to engage the respective hook or loop fasteners positioned underneath the stretch covers such that each hook and loop connection is concealed underneath the stretch covers.

The pocketed sling 26 is sewn or otherwise shaped to define a pocket for holding the removable absorbent pad 28 therein. For example, the pocketed sling may include a cuff partially or completely extending around the periphery of the sling, a main sling layer, and a pocket formed between the cuff and main sling layer. The opening of the pocket may be further rimmed with elastic to allow the pocket opening to be stretched open to insert or remove the absorbent pad 28. In certain aspects, the pocketed sling includes two pockets 80, 81 positioned at opposite ends of the sling in which one pocket 80 is configured to align and attach to the front end of the outer diaper 24 while the other pocket 81 is configured to align and attach to the back end of the outer diaper. In certain aspects, the pocketed sling 26 may have the absorbent pad integrally formed within the sling, and in other aspects, the pocketed sling 26 is configured to receive a removable absorbent pad. For example, the removable absorbent pad 28 may be positioned on the main sling layer, and each pocket 80, 81 may be configured to receive and retain an end portion of the absorbent pad such that the absorbent pad remains immobile within the pocketed sling while in use.

In certain aspects, the absorbent pad 28 is the primary component for urine and fecal containment, the pocketed sling 26 is the secondary component for containment, and the diaper 24 is the tertiary component. The absorbent pad may preferably include an antibacterial or antimicrobial textile fabric, such as fabrics that can include fibers can then be used in knits, wovens or nonwoven fabrics as either a filament or spun yarn. In certain aspects, these antibacterial or antimicrobial fabrics may include, for example, an antimicrobial agent selected from the group consisting of copper, copper salts, silver, silver salts, nickel, nickel salts, or any combination thereof. The absorbent pad may be either partially or completely made with the antibacterial or antimicrobial textile fabric thereby minimizing the presence and/or growth of bacteria and microbes in the absorbent pad.

By constructing the diaper 20 such that the absorbent pad 28, pocketed sling 26, and outer diaper 24 are detachable, one or more of the components can be detached/removed, laundered, and/or disposed of based on the degree of soiling. In certain aspects, the absorbent pad 28 may include a center portion having padding, side sections flanking the center portion extending the length of the absorbent pad, and flexible strips positioned on opposite ends of the pad. These flexible strips may be thinner than the center portion of the absorbent pad and are configured to engage and be retained by the pocket 80, 81 of the pocketed sling. Advantageous results may be achieved by employing absorbent pads with varied thicknesses. For example, thickness may be varied about the longitudinal axis and/or in a widthwise direction of the absorbent pad to adequately and comfortably engage the wearer.

In certain aspects, a center portion of the absorbent pad may be quilted to reduce the thickness of the absorbent pad. By reducing the thickness of the central portion, the thickness of side sections surrounding this central portion can be greater so that the volume of fluid that can be absorbed can be relatively large without increasing the bulk of the absorbent pad to a degree that it would cause discomfort to the wearer. These side sections may be made from knits, wovens, or nonwoven fabric, and these side sections may include, for example, blends of rayon and polyester or viscose or a micro terry fabric including one hundred percent micro terry fabrics.

Most fluid absorbent materials (and/or reusable fluid absorbent materials) tend to easily collapse and not retain shape after a few uses, which may lead to bunching. Bunching is especially problematic in reusable pads because, bunched pads may not be adequately cleaned when laundering. For example, fecal matter or urine may be inadvertently retained in the bunched pad even after laundering. To potentially avoid this problem, the disclosed fluid absorbent pad may be provided with additional structural integrity by including, for example, overlock stitches formed along the longitudinal edges of the central portion and the side sections of the pad. Particularly, lateral overlock stitches extending along the ends of pad may be included, which will advantageously provide peripheral stiffness to reduce or prevent bunching, without interfering with either the softness or the fluid retention characteristics of the pad. When the pads are removed and laundered, the peripheral stiffness added by the overlock stitches will tend to help separate the pad sections to promote more thorough cleaning, since there will be a greater likelihood that all surfaces will be exposed.

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claim.

What is claimed is:

1. A diaper assembly, comprising:
    a diaper including hook fasteners concealed from view beneath covers constructed from resiliently stretchable material, the hook fasteners including a single elongate hook fastener attached to an underside of a single elongate cuff located near a front of the diaper, and two spaced apart hook fasteners attached to the diaper and concealed from view beneath corresponding respective rear covers located near a rear of the diaper; and a pocketed sling configured to removably attach to the diaper, the pocketed sling including a pocket portion, an elongate loop fastener located at a front of the pocket portion and facing in a direction away from the diaper for removably attaching to the single elongate hook fastener attached to the underside of the single elongate cuff, and left and right laterally extending tabs extending outwardly from the pocket portion, the laterally extending tabs carrying loop fasteners facing the diaper for removably attaching to the two spaced apart hook fasteners on the diaper beneath the rear covers, thereby concealing attachment points between the diaper and the pocketed sling while holding the pocket portion open.

2. The diaper assembly of claim 1, further comprising a removable absorbent pad retained within the pocket portion of the pocketed sling.

3. The diaper assembly of claim 1, wherein the pocketed sling comprises an absorbent pad integrally formed within the pocketed sling.

4. The diaper assembly of claim 3, wherein the pocketed sling comprises a pocket formed on a front end of the pocketed sling and the rear end of the pocketed sling and each pocket includes the left and right laterally extending tabs carrying loop fasteners thereon arranged to removably attach to the hook fasteners of the outer diaper beneath the covers.

5. The diaper assembly of claim 1, wherein the diaper includes at least one cover positioned on opposite sides of a same end of the diaper.

6. The diaper assembly of claim 1, wherein the diaper includes a pair of covers at one end thereof and a single elongate cover at the opposing end thereof.

7. The diaper assembly of claim 1, wherein each of the covers are constructed from woven or non-woven material.

8. The diaper assembly of claim 7, wherein the woven or non-woven material comprises nylon, rayon, cotton, polyester, a polyurethane-polyurea copolymer, or any combination thereof.

9. The diaper assembly of claim 1, wherein the pocketed sling comprises a first pocket formed on a front end of the pocketed sling and a second pocket formed on a rear end of the pocketed sling in which at least one of the pockets includes the left and right laterally extending tabs carrying loop fasteners thereon arranged to removably attach to the hook fasteners of the diaper beneath the covers.

10. The diaper assembly of claim 1, wherein the pocketed sling includes a cuff extending around the periphery of the sling, a main sling layer, and a pocket formed between the cuff and main sling layer.

11. The diaper assembly of claim 1, wherein the pocketed sling includes a cuff extending around the periphery of the sling, a main sling layer, and two pockets formed between the cuff and main sling layer.

* * * * *